United States Patent
Zhong et al.

(10) Patent No.: US 7,166,743 B2
(45) Date of Patent: *Jan. 23, 2007

(54) METHODS OF MAKING INTERMEDIATES FROM POLYHYDROXYALKANOATES

(75) Inventors: Luhua Zhong, Woburn, MA (US); Robert S. Whitehouse, Lexington, MA (US)

(73) Assignee: Metabolix, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/098,227

(22) Filed: Apr. 4, 2005

(65) Prior Publication Data

US 2005/0182235 A1    Aug. 18, 2005

Related U.S. Application Data

(63) Continuation of application No. 10/326,442, filed on Dec. 18, 2002, now Pat. No. 6,897,338.

(60) Provisional application No. 60/402,469, filed on Aug. 9, 2002, provisional application No. 60/341,546, filed on Dec. 18, 2001.

(51) Int. Cl.
C07C 51/00 (2006.01)

(52) U.S. Cl. .................................................. 562/599

(58) Field of Classification Search ..................... None
See application file for complete search history.

(56) References Cited

U.S. PATENT DOCUMENTS

| | | | |
|---|---|---|---|
| 2,361,036 A | 10/1944 | Kung | 260/526 |
| 3,859,386 A | 1/1975 | Mainord | 260/878 R |
| 4,031,115 A | 6/1977 | Kurkov | 260/343.6 |
| 4,101,533 A | 7/1978 | Lafferty et al. | 528/491 |
| 4,129,711 A | 12/1978 | Viout et al. | 526/286 |
| 4,193,896 A | 3/1980 | Cook | 260/2.3 |
| 4,230,643 A | 10/1980 | Eichhorn et al. | 525/253 |
| 4,234,907 A | 11/1980 | Daniel | 362/32 |
| 4,309,357 A | 1/1982 | Chiusoli et al. | 260/413 |
| 4,324,880 A | 4/1982 | Dhein et al. | 528/80 |
| 4,365,088 A | 12/1982 | Vanlautem et al. | 562/579 |
| 4,435,534 A | 3/1984 | Jones et al. | 524/292 |
| 4,465,634 A | 8/1984 | Chiusoli et al. | 260/413 |
| 4,489,188 A | 12/1984 | Jones et al. | 524/292 |
| 4,525,512 A | 6/1985 | Hudson | 524/284 |
| 4,649,170 A | 3/1987 | Reid | 524/247 |
| 4,876,331 A | 10/1989 | Doi | 528/361 |
| 4,876,368 A | 10/1989 | Broussard et al. | 549/374 |
| 4,910,145 A | 3/1990 | Holmes et al. | 435/259 |
| 4,935,052 A | 6/1990 | Huppatz et al. | 71/105 |
| 4,968,611 A | 11/1990 | Traussnig et al. | 435/135 |
| 4,997,976 A | 3/1991 | Brunengraber et al. | 560/189 |
| 5,066,657 A | 11/1991 | Hayashi et al. | 514/269 |
| 5,107,016 A | 4/1992 | Pennetreau | 560/179 |
| 5,112,865 A | 5/1992 | Nichels et al. | 514/546 |
| 5,141,924 A | 8/1992 | Bolin | 514/12 |
| 5,145,989 A | 9/1992 | Dougherty et al. | 560/205 |
| 5,186,744 A | 2/1993 | Bodwell et al. | 106/243 |
| 5,213,976 A | 5/1993 | Blauhut et al. | 435/135 |
| 5,229,528 A | 7/1993 | Brake et al. | 549/274 |
| 5,236,987 A | 8/1993 | Arendt | 524/287 |
| 5,245,023 A | 9/1993 | Peoples et al. | 536/23.2 |
| 5,250,430 A | 10/1993 | Peoples et al. | 435/232 |
| 5,264,614 A | 11/1993 | Brake | 560/179 |
| 5,270,147 A | 12/1993 | Van Thillo et al. | 430/262 |
| 5,286,842 A | 2/1994 | Kimura | 528/354 |
| 5,292,860 A | 3/1994 | Shiotani et al. | 528/361 |
| 5,352,763 A | 10/1994 | Yamaguchi et al. | 528/361 |
| 5,455,221 A | 10/1995 | Cutler et al. | 504/291 |
| 5,461,139 A | 10/1995 | Gonda et al. | 528/361 |
| 5,480,794 A | 1/1996 | Peoples et al. | 435/232 |
| 5,512,669 A | 4/1996 | Peoples et al. | 536/23.2 |
| 5,516,883 A | 5/1996 | Hori et al. | 528/354 |
| 5,534,432 A | 7/1996 | Peoples et al. | 435/240.4 |
| 5,563,239 A | 10/1996 | Hubbs et al. | 528/361 |
| 5,665,831 A | 9/1997 | Neuenschwander et al. | 525/415 |
| 5,750,751 A | 5/1998 | Saam | 554/165 |
| 5,879,669 A | 3/1999 | Clausen et al. | 424/70.11 |
| 5,894,062 A | 4/1999 | Liddell | 435/135 |
| 5,928,781 A | 7/1999 | Caines et al. | 428/341 |
| 5,942,597 A | 8/1999 | Noda et al. | 528/361 |

(Continued)

FOREIGN PATENT DOCUMENTS

EP    A 0 069 497    1/1983

(Continued)

OTHER PUBLICATIONS

Bohmert et al., "Transgenic Arabidopsis plants can accumulate polyhydroxybutyrate to up to 4% of their fresh weight", *Planta*, 211, 841-845 (2000).

(Continued)

*Primary Examiner*—Paul A. Zucker
(74) *Attorney, Agent, or Firm*—Fish & Richardson P.C.

(57) ABSTRACT

Methods of forming acrylic acid by heating a PHA are disclosed. The PHA can be derived from a biomass of a non-fossil source. The PHA can be, for example, poly 3-hydroxypropionate or a 3-hydroxypropionate containing polymer. The methods can include, for example, heating the PHA to a temperature of at least about 100° C. to form acrylic acid.

15 Claims, No Drawings

U.S. PATENT DOCUMENTS

| | | | | |
|---|---|---|---|---|
| 6,008,184 | A | 12/1999 | Pluyter et al. | 510/524 |
| 6,043,063 | A | 3/2000 | Kurdikar et al. | 435/135 |
| 6,087,471 | A | 7/2000 | Kurdikar et al. | 528/480 |
| 6,110,998 | A | 8/2000 | Slinkard et al. | 524/108 |
| 6,897,338 | B2 * | 5/2005 | Zhong et al. | 562/599 |

FOREIGN PATENT DOCUMENTS

| | | |
|---|---|---|
| EP | A 0 392 687 | 10/1990 |
| GB | 1120427 | 7/1968 |
| JP | 3231904 | 10/1991 |
| JP | 6087784 | 3/1994 |
| WO | WO 94/11440 | 5/1994 |
| WO | WO 98/36078 | 8/1998 |
| WO | WO 98/39453 | 9/1998 |
| WO | WO 98/46782 | 10/1998 |
| WO | WO 99/14313 | 3/1999 |
| WO | WO 99/61624 | 12/1999 |
| WO | WO 99/64078 | 12/1999 |
| WO | WO 00/08198 | 2/2000 |

OTHER PUBLICATIONS

Braunegg, G. et al., "A Rapid Gas Chromatographic Method for the Determination of Poly-β-hydroxybutyric Acid in Microbial Biomass", *Eur. J. Applied Microbiology and Biotechnolgy*, vol. 6, No. 1, pp. 29-37 (1978).

Byrom, "Miscellaneous Biomaterials", *Biomaterials*, pp. 333-359 (MacMillan Publishers, London 1991).

Clarke, J.B. et al., "Waterborne Coatings and Additives", D.R. Kasa and W.D. Davies editors, *The Royal Society of Chemistry*, Publication No. 195, p. 18 (1995).

Comeau et al., "Determination of poly-β-Hydroxybutyrate and Poly-β-Hydroxyvalerate in Activated Sludge by Gas-liquid Chromatography", *Applied and Environmental Microbiology*, vol. 54, No. 9, pp. 2325-2327 (Sep. 1988).

Doi, Y., *Microbial Polyesters*, VCH, Weinheim (1990).

Grassie et al., "The Thermal Degradation of Poly(-(D)-β-Hydroxybutyric Acid): Part 1-Identification and Quantitative Analysis of Products", *Polymer Degradation and Stability*, 6, 47-61 (1984).

Hocking et al., "Biopolyesters", *Chemistry and Technology of Biodegradable Polymers*, pp. 48-96 (Chapman & Hall, London 1994).

Holmes, "Biologically Produced (R)-3-hydroxy-alkanoate Polymers and Copolymers", *Developments in Crystalline Polymers*, (Basset, ed.) vol. 2, pp. 1-65, (Elsevier, London 1988).

Huijberts et al., "Gas-Chromatographic Analysis of Poly(3-Hydroxyalkanoates) in Bacteria", *Biotechnology Techniques*, vol. 8, No. 3, pp. 187-192 (Mar. 1994).

Jan et al., "Study of Parameters affecting Poly(3-Hydroxybutyrate) Quantification by Gas Chromatography", *Analytical Biochemistry* 225, pp. 258-263 (1995).

Kunioka et al., "Thermal Degradation of Microbial Copolyesters: Poly(3-hydroxybutyrate-co-3-hydroxyvalerate) and Poly(3-hydroxybutyrate-co-4-hydroxybutyrate)", *Macromolecules*, vol. 23, No. 7, pp. 1933-1936 (1990).

Lee et al., "Production of Poly(3-Hydroxybutyrate-co-3-Hydroxyhexanoate) by High-Cell-Density Cultivation of Aeromonas Hydrophila", *Biotechnology and Bioengineering*, 67: 240-244 (2000).

Lehrle et al., "Thermal Degradation of Bacterial Poly(hydroxybutyric acid): Mechanisms from the Dependence of Pyrolysis Yields on Sample Thickness", *Macromolecules*, vol. 27, No. 14, pp. 3782-3789 (1994).

Matsusaki et al., "Biosynthesis and Properties of Poly(3-hydroxybutyrate-co-3-hydroxyalkanoates) by Recombinant Strains of Pseudomonas sp. 61-3", *Biomacromolecules*, 1: 17-22 (2000).

Mitomo, "Aminolysis of Poly (β-Hydroxybutyrate) and its Copolymer", *Sen-1-Gakkaishi*, vol. 48 No. 11, 595-601 (1992).

Morikawa et al., "Pyrolysis of bacterial polyalkanoates" *Canadian Journal of Chemistry*, vol. 59, No. 15, pp. 2306-2313 (Aug. 1, 1981).

Müller et al., "Poly(hydroxyalkanoates): A Fifth Class of Physiologically Important Organic Biopolymers?**", *Angewandte Chemie*, vol. 32, No. 3, pp. 477-502 (Mar. 1993).

Nawrath et al., "Targeting of the polyhydroxybutyrate biosynthetic pathway to the plastids of Arabidopsis thalian results in high levels of polymer accumulation", *Proceedings of the National Academy of Sciences*, vol. 91, No. 26, pp. 12760-12764 (Dec. 20, 1994).

Park et al., "Production of Poly(3-hydroxybutyrate-co-3-hydroxyhexanoate) by Metabolically Engineered *Escherichia coli* Strains", *Biomacromolecules*, vol. 2, No. 1, pp. 248-1254 (2001).

Riis et al., "Gas chromatographic determination of poly-βhydroxybutyric acid in microbial biomass after hydrochloric acid propanolysis", *Journal of Chromatography*, vol. 445, pp. 285-289 (1988).

Steinbuchel, "Polyhydroxyalkanoic Acids" *Biomaterials* (Byrom, ed.) pp. 123-213 (MacMillan Publishers, London 1991).

Valentin et al., "PHA production, from bacteria to plans", *International Journal of Macromolecules*, 25, 303-306 (1999).

Veech et al., "Ketone Bodies, Potential Therapeutic Uses", *IUMB Life*, 51: 241-247 (2001).

Williams et al., "Biodegradable plastics from plants", *Chemtech*, 26:38-44 (1996).

Xanthos et al., "Solvolysis", *Frontiers in the Science and Technology of Polymer Recycling*, pp. 425-436 (1998).

* cited by examiner

METHODS OF MAKING INTERMEDIATES FROM POLYHYDROXYALKANOATES

CROSS-REFERENCE TO RELATED APPLICATIONS

Under 35 U.S.C. §120, this application is a continuation of and claims priority to U.S. Utility Patent Application Serial No.: 10/326,442, filed Dec. 18, 2002, now U.S. Pat. No. 6,897,338, and entitled "Methods of Making Chemical Intermediates From Polyhydroxyalkanoates," which claims priority under 35 U.S.C. §119(e)(1) to U.S. Provisional Patent Application Ser. No. 60/341,546, filed Dec. 18, 2001, and entitled "Process of Making Chemical Intermediates from Naturally Occurring Polyhydroxyalkanoates," and to U.S. Provisional Patent Application Ser. No. 60/402,469, filed Aug. 9, 2002, and entitled "Alkanoic and Alkenoic Acid Esters and Methods of Making Same. The contents of all parent applications are incorporated by reference.

TECHNICAL FIELD

The invention generally relates to methods of making intermediates from polyhydroxyalkanoates (PHAs).

BACKGROUND

Various chemical intermediates, such as esters, amides, diols and acids, are known to be useful. For example, certain chemical intermediates can be used as solvents (e.g., coalescing solvents, cleaning solvents), process additives, plasticizers, surface active agents, in the formulation of products (e.g., industrial products, consumer products), and/or monomers in a polymerization process.

SUMMARY

The invention generally relates to methods of making intermediates from PHAs.

In one aspect, the invention features a method. The method includes treating a biomass containing a PHA to form a PHA intermediate, and removing at least about 10 weight percent of the PHA intermediate from the biomass.

In another aspect, the invention features a method that includes contacting a PHA with an aprotic catalyst to form an ester. The ester has only one monomer unit from the PHA.

In a further aspect, the invention features a method that includes treating a PHA-containing non-lyophilized biomass to form an ester, and removing at least some of the ester from the biomass.

In one aspect, the invention features a method that includes combining a PHA with an alcohol to form an ester. The PHA and the alcohol form a combination containing less than about one milliliter of solvent other than the alcohol per gram of PHA.

In another aspect, the invention features a method that includes combining a PHA and an alcohol to form an ester from a PHA. The percent yield of the ester is at least about 50%, and a ratio of the moles of the alcohol per mole of PHA monomer unit is less than about 20.

In a further aspect, the invention features a method that includes heating a PHA to a temperature of at least about 180° C. to form an ester.

In one aspect, the invention features a method that includes treating a PHA to form an amide. The amide has only one repeat unit from the PHA.

In another aspect, the invention features a method that includes treating a biomass containing a PHA to form an amide.

In a further aspect, the invention features a method that includes heating a PHA to a temperature of at most about 90° C. to form an amide. The percent yield of the amide is at least about 50%.

In one aspect, the invention features a method that includes heating a PHA to form a cyclic amide.

In another aspect, the invention features a method that includes hydrogenolyzing a PHA to form a diol.

In one aspect, the invention features a method that includes heating a biomass containing a PHA to form an alkenoic acid. The percent yield of alkenoic acid from the PHA is at least about 50%.

In another aspect, the invention features a method that includes heating a PHA to a temperature of at least about 200° C. to form an alkenoic acid.

In a further aspect, the invention features a method that includes treating a PHA to form acrylic acid. The PHA has at least one 3-hydroxypropionate monomer.

In one aspect, the invention features a method. The method includes heating a mixture containing a first portion of a PHA to form a first portion of an alkenoic acid, and adding, after forming the first portion of the alkenoic acid, a second portion of the PHA to the mixture.

The methods can further include using the intermediate(s) (e.g., as a solvent, as a process additive, as a monomer to form a polymer, and/or in the formulation of a product).

In certain embodiments, the methods can be relatively nontoxic, relatively environmentally friendly, relatively sustainable, relatively simple and/or relatively inexpensive.

In some embodiments, the intermediates can be formed at relatively high yield.

In certain embodiments, the methods can result in the formation of a chiral intermediate. This can be advantageous, for example, if the usefulness (e.g., commercial usefulness) of the intermediate depends on the chirality of the intermediate.

In some embodiments, the PHAs can serve as non-fossil carbon based feedstocks for materials (PHA intermediates).

Features, aspects and advantages of the invention are in the description and claims.

DETAILED DESCRIPTION

In general, the methods include treating a PHA to form a PHA intermediate. The methods optionally include using the PHA intermediate (e.g., as a solvent, as a process additive, as a monomer to form a polymer, a precursor to form another product, and/or in the formulation of a product).

A PHA contains multiple monomer units. Typically, a PHA contains at least about 500 monomer units (e.g., at least about 1,000 monomer units). In some embodiments, when a PHA is a homopolymer, the multiple monomer units contained in the PHA are all the same. In certain embodiments, when the PHA is a copolymer, the multiple monomer units contained in the PHA include at least two different monomer units.

A PHA intermediate is a compound that has fewer monomer units than present in the PHA from which the PHA intermediate was formed. In some embodiments, a PHA intermediate contains only one monomer unit from the PHA. In certain embodiments, a PHA intermediate can contain multiple monomer units (e.g., from two monomer units to 500 monomer units, from two monomer units to 400 monomer units, from two monomer units to 300 monomer units, from two monomer units to 200 monomer units, from two monomer units to 100 monomer units, from two monomer units to 50 monomer units, from two monomer units to 40 monomer units, from two monomer units to 25 monomer units), but the PHA intermediate contains fewer monomer units than present in the PHA itself. Examples of PHA intermediates include esters, amides, diols and acids.

As explained below, treating a PHA to form a PHA intermediate generally includes heating the PHA under appropriate conditions (e.g., in the presence of a reactant, in the presence of a solvent, in the presence of a catalyst, and/or at elevated pressure).

In some embodiments, the methods result in a relatively high yield of the PHA intermediate. For example, the percent yield of PHA intermediate from the PHA can be at least about 30% (e.g., at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%). The percent yield of a PHA intermediate from a PHA is determined as follows. The number of moles of the PHA intermediate is multiplied by the number of monomer units per mole of the PHA intermediate, which provides a value A. The number of moles of PHA is multiplied by the number of monomer units per mole of PHA, which provides a value B. The value A is divided by the value B to provide a value C, which is multiplied by 100%.

In embodiments in which a chiral PHA is treated to form a chiral PHA intermediate, the percent chirality yield of the chiral PHA intermediate can be relatively high. For example, the percent chirality yield of a chiral PHA intermediate from a chiral PHA can be at least about five percent (e.g., at least about 10%, at least about 25%, at least about 50%, at least about 75%, at least about 85%, at least about 90%, at least about 95%, at least about 98%). The percent chirality yield of a chiral PHA intermediate from a chiral PHA is determined as follows. The number of moles of the chiral PHA intermediate is multiplied by the number of chiral monomer units per mole of the chiral PHA intermediate, which provides a value D. The number of moles of chiral PHA is multiplied by the number of chiral monomer units per mole of the chiral PHA, which provides a value E. The value D is divided by the value E to provide a value F, which is multiplied by 100%.

As used herein, the term chiral PHA refers to a PHA in which at least some of the monomer units are chiral, and all the chiral monomer units in the PHA have the same chirality (e.g., R configuration or S configuration). As used herein, the term chiral PHA intermediate refers to a PHA intermediate that is formed from a chiral PHA and that has the same chirality as the chiral monomer units in the chiral PHA.

In certain embodiments in which the PHA is derived from biomass and at least some of the PHA is not removed from the biomass before being treated to form the PHA intermediate, the methods can include removing at least a portion of the PHA intermediate from the biomass. For example, at least about 10 weight percent (e.g., at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 98 weight percent) of the PHA intermediate can be removed from the biomass.

PHAs

In certain embodiments, a PHA has at least one monomer unit with the structure:

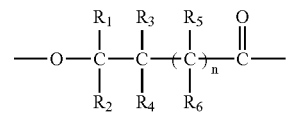

n is zero or an integer (e.g., one, two, three, four, five, six, seven, eight, nine, 10, 11, 12, 13, 14, 15, etc.). Each of $R_1$, $R_2$, $R_3$, $R_4$, $R_5$ and $R_6$ is independently a hydrogen atom, a halogen atom or a hydrocarbon radical. A hydrocarbon radical contains at least one carbon atom (e.g., one carbon atom, two carbon atoms, three carbon atoms, four carbon atoms, five carbon atoms, six carbon atoms, seven carbon atoms, eight carbon atoms, etc.). A hydrocarbon radical can be saturated or unsaturated, substituted or unsubstituted, branched or straight chained, and/or cyclic or acyclic. Examples of substituted hydrocarbon radicals include halo-substituted hydrocarbon radicals, hydroxy-substituted hydrocarbon radicals, nitrogen-substituted hydrocarbon radicals and oxygen-substituted hydrocarbon radicals. Examples of hydrocarbon radicals include methyl, ethyl, propyl, butyl, pentyl, hexyl, octyl and decyl.

Examples of monomer units include 3-hydroxybutyrate, 3-hydroxypropionate, 3-hydroxyvalerate, 3-hydroxyhexanoate, 3-hydroxyheptanoate, 3-hydroxyoctanoate, 3-hydroxynonaoate, 3-hydroxydecanoate, 3-hydroxydodecanoate, 3-hydroxytetradecanoate, 3-hydroxyhexadecanoate, 3-hydroxyoctadecanoate, 4-hydroxybutyrate, 4-hydroxyvalerate, 5-hydroxyvalerate, and 6-hydroxyhexanoate.

In some embodiments, a PHA can be a homopolymer (all monomer units are the same). Examples of PHA homopolymers include poly 3-hydroxyalkanoates (e.g., poly 3-hydroxypropionate, poly 3-hydroxybutyrate, poly 3-hydroxyhexanoate, poly 3-hydroxyheptanoate, poly 3-hydroxyoctanoate, poly 3-hydroxydecanoate, poly 3-hydroxydodecanoate), poly 4-hydroxyalkanoates (e.g., poly 4-hydroxybutyrate), poly 5-hydroxyalkanoates (e.g., poly 5-hydroxypentanoate), poly 6-hydroxyalkanoates (e.g., poly 6-hydroxyhexanoate) and polylactic acid. Another example of a homopolymer of interest is polyglycolic acid (for which there is only one carbon other than the carbonyl carbon in the monomer structure).

In certain embodiments, a PHA can be a copolymer (contain two or more different monomer units). Examples of PHA copolymers include poly 3-hydroxybutyrate-co-3-hydroxypropionate, poly 3-hydroxybutyrate-co-3-hydroxyvalerate, poly 3-hydroxybutyrate-co-3-hydroxyhexanoate, poly 3-hydroxybutyrate-co-4-hydroxybutyrate, poly 3-hydroxybutyrate-co-4-hydroxyvalerate, poly 3-hydroxybutyrate-co-6-hydroxyhexanoate, poly 3-hydroxybutyrate-co-3-hydroxyheptanoate, poly 3-hydroxybutyrate-co-3-hydroxyoctanoate, poly 3-hydroxybutyrate-co-3-hydroxydecanoate, poly 3-hydroxybutyrate-co-3-hydroxydodecanotate, poly 3-hydroxybutyrate-co-3-hydroxyoctanoate-co-3-hydroxydecanoate, poly 3-hydroxydecanoate-co-3-hydroxyoctanoate, and poly 3-hydroxybutyrate-co-3-hydroxyoctadecanoate. Although examples of PHA copolymers having two different monomer units have been provided, a PHA can have more than two different monomer units (e.g., three different monomer units, four different monomer units, five different monomer units, six different monomer units, seven different monomer units, eight different monomer units, nine different monomer units, etc.).

In certain embodiments, the PHA is derived from biomass, such as plant biomass and/or microbial biomass (e.g., bacterial biomass, yeast biomass, fungal biomass). Biomass-derived PHA can be formed, for example, via enzymatic polymerization of the monomer units. Typically, the biomass is non-lyophilized. The biomass can be formed of one or more of a variety of entities. Such entities include, for example, microbial strains for producing PHAs (e.g., *Alcaligenes eutrophus* (renamed as *Ralstonia eutropha*), *Alcaligenes latus, Azotobacter, Aeromonas, Comamonas, Pseudomonads*), genetically engineered organisms, preferably containing no recombinant plasmids, for producing PHAs (e.g., *Pseudomonas, Ralstonia, Escherichia coli, Klebsiella*), yeasts for producing PHAs, and plant systems for producing PHAs. Such entities are disclosed, for example, in Lee, *Biotechnology & Bioengineering* 49:1–14 (1996); Braunegg et al., (1998), J. Biotechnology 65: 127–161; Madison, L. L. and Huisman, G. W. (1999), Metabolic Engineering of Poly(3-Hydroxyalkanoates): From DNA to Plastic. Microbiol. Mol. Biol. Rev. 63, 21–53; and Snell and Peoples 2002, Metabolic Engineering 4: 29–40, which are hereby incorporated by reference.

In some embodiments in which the PHA is derived from biomass, most of the PHA that is treated to form the PHA intermediate is not removed from the biomass before being treated to form the intermediate. For example, in certain embodiments, less than about 50 weight percent (e.g., less than about 40 weight percent, less than about 30 weight percent, less than about 20 weight percent, less than about 10 weight percent, less than about weight percent five weight percent, less than about three weight percent, less than about one weight percent, about zero weight percent) of the PHA that is treated to form the PHA intermediate is removed from the biomass before being treated to form the PHA intermediate.

In certain embodiments in which the PHA is derived from biomass, most of the PHA that is treated to form the PHA intermediate is removed from the biomass before being treated to form the PHA intermediate. For example, in some embodiments, at least about 60 weight percent (at least about 70 weight percent, at least about 80 weight percent, at least about 90 weight percent, at least about 95 weight percent, at least about 98 weight percent, about 100 weight percent) of the PHA that is treated to form the PHA intermediate is removed from the biomass before being treated to form the PHA intermediate.

Esters

Treating a PHA to form an ester (e.g., an alkanoic acid ester, an alkenoic acid ester) generally includes combining the PHA with an alcohol (e.g., a monohydric alcohol, a polyhydric alcohol) and optionally a catalyst (e.g., a protic catalyst, an aprotic catalyst), and exposing the PHA to elevated temperature and/or elevated pressure.

The alcohol can be represented by the structure $R_7OH$, where $R_7$ is a hydrocarbon radical that contains one or more carbon atoms (e.g., one carbon atom, two carbon atoms, three carbon atoms, four carbon atoms, five carbon atoms, six carbon atoms, seven carbon atoms, eight carbon atoms, etc.). $R_7$ can be saturated or unsaturated, substituted or unsubstituted, branched or straight chained, and/or cyclic or acyclic. Examples of substituted hydrocarbon radicals include halo-substituted hydrocarbon radicals, hydroxy-substituted hydrocarbon radicals, nitrogen-substituted hydrocarbon radicals and oxygen-substituted hydrocarbon radicals. Examples of hydrocarbon radicals include methyl, ethyl, propyl, butyl, 2-ethylhexyl, isopropyl, isobutyl, tertiary butyl, hexyl, octyl, cyclohexyl, decyl, dodecyl, stearyl, oleyl, linolyl and linolenyl.

Examples of alcohols include methanol, ethanol, propanol, butanol, 2-ethylhexanol, cyclohexanol, decyl alcohol, dodecyl alcohol, isopropyl alcohol, isobutyl alcohol, dodecyl alcohol, stearyl alcohol, oleyl alcohol, linolyl alcohol, linolenyl alcohol, propylene glycol, glycerol, ethylene glycol, propylene glycol, 1,2-propane diol, 1,3-propane diol, 1,3-butane diol, 1,4-butane diol, 1,6-hexane diol, glycerol, erythritol, pentaerythritol, dipentaerythritol, thrimethylol propane, xylose, sucrose, dextrose and triethanolamine.

In certain embodiments, an ester formed by treating the PHA is an alkanoic acid ester. In some embodiments, an alkenoic acid ester can be represented by the structure:

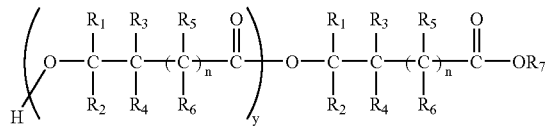

y is less than the number of monomer repeat units in the PHA. In some embodiments, y is from one to 499 (e.g., from one to 399, from one to 299, from one to 199, from one to 99, from one to 49, from one to 39, from one to 24). In certain embodiments, y is zero.

Examples of alkanoic acid esters include methyl 3-hydroxybutyrate, ethyl 3-hydroxybutyrate, methyl 3-hydroxypropionate, ethyl 3-hydroxy propionate, methyl 4-hydroxybutyrate, ethyl 4-hydroxybutyrate, cyclohexyl 3-hydroxybutyrate, cyclohexyl 4-hydroxybutyrate, stearyl 4-hydroxybutyrate and stearyl 3-hydroxybutyrate.

In some embodiments, an ester formed by treating a PHA is an alkenoic acid ester. In certain embodiments, an alkenoic acid ester can be represented by the structure:

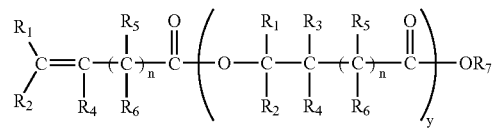

Without wishing to be bound by theory, it is believed that alkenoic acid esters can be formed, for example, in a dehydration reaction that can occur prior or subsequent to alcoholysis of the PHA or PHA intermediate ester bond, resulting in formation of one or more carbon-carbon double bonds. In certain embodiments (e.g., when n is zero), alkenoic acid esters are formed when one or more of $R_1$, $R_2$, $R_3$ and $R_4$ (e.g., one or both of $R_3$ and $R_4$) is a hydrogen atom.

Examples of alkenoic acid esters include ethyl crotonate, methyl crotonate, butyl crotonate, 2-ethyl hexyl crotonate, ethyl 2-octenoate and ethyl 2 pentenoate.

As noted above, the ester is generally formed by combining the PHA with an alcohol, and exposing the PHA to elevated temperature and/or elevated pressure.

In general, the amount of alcohol used can be selected as desired. In certain embodiments (e.g., when it is desirable to form an ester for which y=0), at least about one mole (e.g., at least about two moles, at least about four moles) of alcohol is used per mole of monomer unit in the PHA and/or at most about 20 moles (e.g., at most about 10 moles, at most about six moles) of alcohol are used per mole of PHA monomer unit. For example, from about two moles to about 20 moles (e.g., from about two moles to about 10 moles) of alcohol can be used per mole of PHA monomer unit. In some embodiments (e.g., when it is desirable to form ester for which y>0), less than one mole (e.g., less than about 0.9 mole, less than about 0.75 mole, less than about 0.5 moles) of alcohol is used per mole of monomer unit in the PHA.

The temperature can generally be selected as desired. Typically, the temperature greater than about 25° C. In some embodiments, the temperature can be at least about 160° C. (e.g., at least about 170° C., at least about 180° C.). In certain embodiments, the temperature can be at most about 220° C. (e.g., at most about 210° C., at most about 200° C.). For example, the temperature can be from about 160° C. to about 220° C. (e.g., from about 170° C. to about 210° C., from about 170° C. to about 200° C.).

Generally, the pressure can be selected as desired. Typically, the pressure is greater than about 14 psig. In certain embodiments, the pressure can be at least about 50 psig (e.g., at least about 100 psig). In some embodiments, the pressure can be at most about 500 psig (e.g., at most about 250 psig). For example, the pressure can be from about 50 psig to about 500 psig. Typically, elevated pressure is achieved using an inert gas (e.g., nitrogen, helium, argon, krypton, xenon, etc.).

In certain embodiments, the PHA can be treated while using relatively little solvent (e.g., relatively little halogenated solvent) other than the alcohol. For example, the total amount of solvent other than the alcohol present during the treatment of the PHA to form the ester can be less than one milliliter (e.g., less than about 0.9 milliliter, less than about 0.8 milliliter, less than about 0.7 milliliter, less than about 0.6 milliliter, less than about 0.5 milliliter, less than about 0.4 milliliter, less than about 0.3 milliliter, less than about 0.2 milliliter, less than about 0.1 milliliter, less than about 0.05 milliliter, about zero milliliter) per gram of PHA.

In certain embodiments, the amount of undesired byproducts is relatively small. For example, in some embodiments it is desired to form an alkanoic acid ester, alkenoic byproducts can be undesired. In some embodiments, the percent yield of undesirable byproducts (e.g., alkenoic byproducts) from the PHA is less than about 10% (e.g., less than about eight percent, less than about five percent, less than about three percent, less than about one percent).

In some embodiments, the PHA treatment to form the ester is performed in the absence of a catalyst.

In certain embodiments, the PHA treatment to form the ester is performed in the presence of an appropriate catalyst. In general, the catalyst can be a protic catalyst or an aprotic catalyst. Examples of protic catalysts include sulfuric acid, para-toluene sulfonic acid, hydrochloric acid and phosphoric acid. Examples of aprotic catalysts include certain transesterification catalysts (e.g., metal-containing transesterification catalysts), such as, tin compounds (e.g., dibutyltin dilaurate, stannous oxide, dibutyl tin oxide, dibutyl tin chloride), titanium compounds (e.g., tetraalkoxy titanates, ethanolamine complexed with titanium), zinc compounds (e.g., zinc acetate, zinc chloride) and clays (e.g. montmorillonite K10 clay). In some embodiments, more than one catalyst is used.

Generally, in embodiments in which a catalyst is used, the amount of catalyst can be selected as desired. In some embodiments, the catalyst can be at least about 0.1 weight percent (e.g., at least about 0.25 weight percent, at least about 0.5 weight percent, at least about one weight percent) of the total amount of PHA present when the catalyst is added. In certain embodiments, the catalyst can be at most about 10 weight percent (e.g., at most about five weight percent, at most about three weight percent) of the total amount of PHA present when the catalyst is added. For example, the catalyst can be from about 0.1 weight percent to about 10 weight percent (e.g., from about 0.25 weight percent to about five weight percent) of the total amount of PHA present when the catalyst is added.

In some embodiments, while using a relatively small amount of alcohol relative to PHA, an ester can be formed from the PHA at a relatively high percent yield. As an example, while using less than about 20 moles of alcohol per mole of PHA monomer repeat unit, the percent yield of ester from the PHA is at least about 50% (e.g., at least about 60%, at least about 70%, at least about 80%, at least about 90%, at least about 95%, at least about 98%). As another example, while using less than about 10 moles of alcohol per mole of PHA monomer repeat unit, the percent yield of ester is at least about 50% (e.g., at least about 60%, at least about 70%, at least about 80%, at least about 90%, at least about 95%, at least about 98%). As a further example, while using less than about five moles of alcohol per mole of PHA monomer repeat unit, the percent yield of ester from the PHA is at least about 50% (e.g., at least about 60%, at least about 70%, at least about 80%, at least about 90%, at least about 95%, at least about 98%). As an additional example, while using from about one mole of alcohol per mole of PHA monomer repeat unit to about five moles of alcohol per PHA monomer repeat unit, the percent yield of ester from the PHA is at least about 50% (e.g., at least about 60%, at least about 70%, at least about 80%, at least about 90%, at least about 95%, at least about 98%).

The methods can further include isolating at least a portion of the ester formed by treating the PHA. For example, in embodiments in which the PHA is derived from biomass and the PHA is not removed from the biomass before being treated to form the ester, the methods can include removing at least a portion (e.g., at least about 10 weight percent, at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 98 weight percent) of the ester from the biomass.

In embodiments in which the PHA is a PHA copolymer, multiple esters can be formed, corresponding to the different monomer units in the PHA copolymer and the hydrocarbon unit in the alcohol. For example, the PHA can be poly 3-hydroxybutyrate-co-3-hydroxypropionate, the alcohol can be methanol, and the esters can be methyl 3-hydroxybutyrate and methyl 3-hydroxypropionate.

In embodiments in which a PHA homopolymer is combined with different alcohols and treated as described above, multiple esters can be formed, corresponding to the monomer unit contained in the PHA homopolymer and the hydrocarbon units from the alcohols. For example, the PHA can be poly 3-hydroxybutyrate, the alcohols can be methanol and ethanol, and the esters can be methyl 3-hydroxybutyrate and ethyl 3-hydroxybutyrate.

In embodiments in which PHA copolymer is combined with different alcohols, multiple esters can be formed, corresponding to the different monomer units in the PHA copolymer and the different hydrocarbon units in the alcohols. For example, the PHA can be poly 3-hydroxybutyrate-co-3-hydroxypropionate, the alcohols can be methanol and ethanol, and the esters can be methyl 3-hydroxybutyrate, methyl 3-hydroxypropionate, ethyl 3-hydroxybutyrate and ethyl 3-hydroxypropionate.

The esters can be used in various applications. For example, an ester can be used as a chiral synthetic building block (e.g., R-methyl 3-hydroxy butyrate).

As another example, ethyl 3-hydroxybutyrate can be used as a water miscible biodegradable cleaning solvent (e.g., in inks and/or fluxes).

In some embodiments, an ester can serve as a solvent, such as a coalescing solvent (e.g., to promote film from latex compositions, such as paints, which can contain an emulsion or suspension of polymer particles in an aqueous medium). When present in a liquid mixture (e.g., latex composition), the ester can form from about 0.05 weight percent to about 25 weight percent of the mixture. An ester can, for example, reduce a glass transition temperature of composition during the drying and film forming process. An ester can, for example, reduce the volatile organic content in aqueous-based polymer compositions. The esters can, for example, reduce the film forming temperature of a composition. An ester can, for example, evaporate over time (e.g., within about five days) after film formation, and thereby be removed from the film after formation. An ester can, for example, act as an adhesion promoter, and promote the adhesion of solvent based inks (e.g., lithographic inks, gravure inks), solvent based paints or coatings, and/or epoxide based-paints or coatings.

Amides

Treating a PHA to form an amide generally includes combining the PHA with an amine (e.g., a primary amine, a secondary amine), and using elevated temperature and/or pressure.

In general, the amine can be selected as desired. In some embodiments, the amine is an aliphatic primary amine (e.g., an aliphatic primary amine having up to 20 carbon atoms). In certain embodiments, the amine is an oxygen-containing amine (e.g., mono-ethanolamine, di-ethanolamine). In some embodiments, the amine is a diamine (e.g., an ethylene diamine). In certain embodiments, the amine is a cyclic amine. In some embodiments, the amine can be represented by the structure $R_8R_9NH$, where each of $R_8$ and $R_9$ is independently a hydrogen atom or a hydrocarbon radical that contains one or more carbon atoms (e.g., one carbon atom, two carbon atoms, three carbon atoms, four carbon atoms, five carbon atoms, six carbon atoms, seven carbon atoms, eight carbon atoms, etc.). A hydrocarbon radical can be saturated or unsaturated, substituted or unsubstituted, branched or straight chained, and/or cyclic or acyclic. Examples of substituted hydrocarbon radicals include halo-substituted hydrocarbon radicals, hydroxy-substituted hydrocarbon radicals, nitrogen-substituted hydrocarbon radicals and oxygen-substituted hydrocarbon radicals. Examples of hydrocarbon radicals include methyl, ethyl, propyl, butyl, 2-ethylhexyl and 2-hydroxyethyl.

Examples of amines include ammonia, methyl amine, ethyl amine, pyrrolidone, and 2-hydroxyethyl amine.

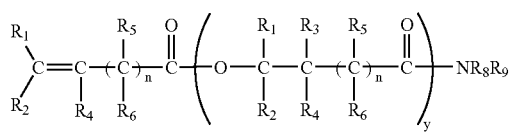

In certain embodiments, an amide formed by treating the PHA is an alkanoic amide. In some embodiments, an alkanoic amide can be represented by the structure:

Examples of alkanoic amides include N-methyl 3-hydroxybutyramide, N-ethyl 3-hydroxybutyramide, N-methyl 4-hydroxybutyramide, N-ethyl 4-hydroxybutyramide, N-hydroxyethyl 4-hydroxybutyramide, 6-hydroxyhexanamide.

In some embodiments, an amide formed by treating a PHA is an alkenoic amide. In certain embodiments, an alkenoic amide can be represented by the structure.

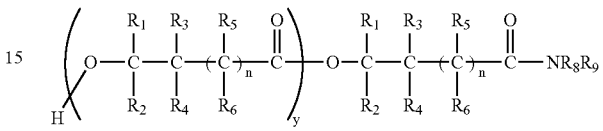

Without wishing to be bound by theory, it is believed that alkenoic amides can be formed, for example, in an elimination reaction which can occur prior or subsequent to aminolysis of the PHA or PHA intermediate ester bond via reactions that involve dehydration, resulting in formation of one or more carbon-carbon double bonds. In certain embodiments, alkenoic amides are formed when one or more of $R_1$, $R_2$, $R_3$ and $R_4$ (e.g., one or both of $R_3$ and $R_4$) is a hydrogen atom. In some embodiments, alkenoic amides are formed when $R_3$ and/or $R_4$ is a hydrogen atom.

Examples of alkenoic amides include acrylamide and methacrylamide.

As noted above, the amide is generally formed by combining the PHA with an amine, and exposing the PHA to elevated temperature and/or elevated pressure.

In general, the amount of amine used can be selected as desired. In certain embodiments (e.g., when it is desirable to form an amide for which y=0), at least about one mole (e.g., at least about 1.5 moles, at least about two moles, at least about three moles) of amine is used per mole of monomer unit in the PHA and/or at most about 20 moles (e.g., at most about 10 moles, at most about five moles) of amine are used per mole of PHA monomer unit. For example, from about 1.5 moles to about 20 moles (e.g., from about 1.5 moles to about five moles) of amine can be used per mole of PHA monomer unit. In some embodiments (e.g., when it is desirable to form amide for which y>0), less than one mole (e.g., less than about 0.9 mole, less than about 0.75 mole, less than about 0.5 moles) of amine is used per mole of monomer unit in the PHA.

The temperature can generally be selected as desired. Typically, the temperature greater than about 25° C. (e.g., at least about 40° C., at least about 50° C., at least about 60° C.). In some embodiments, the temperature can be at most about 100° C. (e.g., at most about 90° C., at most about 80° C.). For example, the temperature can be from about 40° C. to about 90° C. (e.g., from about 50° C. to about 90° C., from about 60° C. to about 90° C.).

Generally, the pressure can be selected as desired. In some embodiments, the pressure is about 14 psig. In certain embodiment, the pressure is greater than about 14 psig (e.g., at least about 50 psig, at least about 100 psig) and/or at most about 500 psig (e.g., at most about 250 psig). For example, the pressure can be from about 50 psig to about 500 psig. Typically, elevated pressure is achieved using nitrogen, although other gases, such as an inert gases, can be used (e.g., helium, argon, krypton, xenon, etc.).

In certain embodiments, the PHA can be treated while using relatively little solvent (e.g., relatively halogenated solvent) other than the amine. For example, the total amount of solvent other than the mine present during the treatment of the PHA to form the amide can be less than one milliliter (e.g., less than about 0.9 milliliter, less than about 0.8 milliliter, less than about 0.7 milliliter, less than about 0.6 milliliter, less than about 0.5 milliliter, less than about 0.4 milliliter, less than about 0.3 milliliter, less than about 0.2 milliliter, less than about 0.1 milliliter, less than about 0.05 milliliter, about zero milliliter) per gram of PHA.

In certain embodiments, the amount of undesired byproducts is relatively low. For example, in some embodiments where alkanoic amides are being prepared, it can be undesirable to form alkenoic byproducts. In some embodiments, the percent yield of undesirable byproducts (e.g., alkenoic byproducts) from the PHA is less than about 10% (e.g., less than about eight percent, less than about five percent, less than about three percent, less than about one percent).

In some embodiments, an amide can be formed from the PHA at a relatively high percent yield. For example, the percent yield of amide from the PHA can be at least about 50% (e.g., at least about 60%, at least about 70%, at least about 80%, at least about 90%, at least about 95%, at least about 98%).

In certain embodiments, an acyclic amide formed via the treatment of a PHA can be further treated to form a cyclic amide (e.g., a lactam). In some embodiments, the cyclic amide has a ring with at least four carbon atoms (e.g., five carbon atoms, six carbon atoms, seven carbon atoms, eight carbon atoms, nine carbon atoms, ten carbon atoms. In some embodiments, a cyclic amide has the following structure:

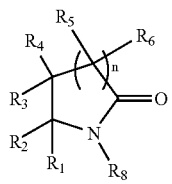

As an example, N-methylpyrrolidone can be formed from N-methyl 4-hydroxybutyramide (e.g., N-methyl 4-hydroxybutyramide formed by treating poly 4-hydroxybutyrate and methylamine). As another example, N-ethylpyrrolidone can be formed from N-ethyl 4-hydroxybutyramide (e.g., ethyl 4-hydroxybutyramide formed by treating formed by treating poly 4-hydroxybutyrate and ethylamine). As another example, N-hydroxyethylpyrrolidone can be formed from N-ethyl 4-hydroxybutyramide (e.g., N-hydroxyethyl 4-hydroxybutyramide formed by treating poly 4-hydroxybutyrate and hydroxyethylamine).

In general, forming a cyclic amide from an acyclic amide includes heating the acyclic amide to a temperature of at least about 100° C. (e.g., at least about 200° C., at least about 250° C., at least about 275° C.) at a pressure of at least about 50 psig (at least about 100 psig, at least about 250 psig, at least about 500 psig) of nitrogen or one or more other gases (e.g., an inert gas, such as helium, argon, krypton, xenon, etc.).

In some embodiments, the percent yield of cyclic amide from acyclic amide is at least about 50% (e.g., at least about 60%, at least about 70%, at least about 80%, at least about 90%, at least about 95%, at least about 98%). In certain embodiments, the percent yield of cyclic amide from the PHA is at least about 50% (e.g., at least about 60%, at least about 70%, at least about 80%, at least about 90%, at least about 95%, at least about 98%).

In some embodiments in which the PHA is derived from biomass, most of the acyclic amide that is formed from the PHA is not removed from the biomass before being treated to form the cyclic amide. For example, in certain embodiments, less than about 50 weight percent (e.g., less than about 40 weight percent, less than about 30 weight percent, less than about 20 weight percent, less than about 10 weight percent, less than about weight percent five weight percent, less than about three weight percent, less than about one weight percent, about zero weight percent) of the acyclic amide that is treated to form the cyclic amide is removed from the biomass before being treated to form the cyclic amide.

The methods can further include isolating at least a portion of the amide formed by treating the PHA. For example, in embodiments in which the PHA is derived from biomass and the PHA is not removed from the biomass before being treated to form the amide, the methods can include removing at least a portion (e.g., at least about 10 weight percent, at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 98 weight percent) of the amide from the biomass.

In embodiments in which the PHA is a PHA copolymer, multiple amides can be formed, corresponding to the monomer unit in the PHA copolymers and the amine. For example, the PHA can be poly 3-hydroxybutyrate-co-3-hydroxypropionate, the amine can be methylamine, and the amides can be N-methyl 3-hydroxybutyramide and N-methyl 3-hydroxypropionamide.

In embodiments in which a PHA homopolymer is combined with different amines and treated as described above to form amides, multiples amides can be formed, corresponding to the monomer unit contained in the PHA homopolymer and the amines. For example, the PHA can be poly 3-hydroxybutyrate, the amines can be methylamine and ethylamine, and the amides can be N-methyl 3-hydroxybutyramide and N-ethyl 3-hydroxybutyramide.

In embodiments in which the PHA is a PHA copolymer and multiple amines are used, multiple amides can be formed, corresponding to the different monomer units in the copolymer and the different amines. For example, the PHA can be poly 3-hydroxybutyrate-co-3-hydroxypropionate, the amines can be methylamine and ethylamine, and the amides can be N-methyl 3-hydroxybutyramide, N-methyl 3hydroxypropionamide, N-ethyl 3-hydroxybutyramide and N-ethyl 3-hydroxypropionamide.

The amides can be used in a variety of applications. For example, N-hydroxyethyl pyrrolidone can be used to produce N-vinyl pyrrolidone, which, in turn, can be used to produce polyvinylpyrrolidone, which can be used, for example, in adhesive applications, as a thickener, and/or as a flocculant. As another example, 3-hydroxypropanamide can be used to produce acrylamide, which, in turn, can be used to produce polyacrylamide, which can be used, for example, in a composition containing moisture absorbing polymers. As a further example, N-methylpyrrolidone can be used as a carrier solvent for paint, ink, adhesive formulations, as a cleaning/degreasing solvent, and/or as a component in paint stripper formulations.

Diols

In general, treating a PHA to form a diol includes hydrogenolyzing the PHA. Typically, this includes heating the PHA in the presence of a reducing species (e.g., reducing agent). Optionally, this can be done in the presence of a solvent and/or a catalyst. In some embodiments, elevated pressure is used (e.g., elevated pressure of hydrogen gas).

Typically, the PHA is heated to a temperature of at least about 100° C. (e.g., at least about 150° C., at least about 160° C.). In some embodiments, the temperature is at most about 260° C. (e.g., at most about 230° C.). For example, the temperature can be from about 100° C. to about 260° C. (e.g., from about 130° C. to about 230° C., from about 160° C. to about 230° C.).

In certain embodiments, a diol formed by treating a PHA has the structure:

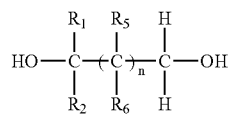

Examples of diols include 1,4-butanediol, 1,3-propanediol, 1,3-butanediol, 1,6-hexanediol, 1,3-pentanediol, 1,3-hexanediol, 1,3-octanediol, 1,2-propanediol, ethylene glycol and propylene glycol.

In embodiments in which a solvent is used, the solvent can generally be selected as desired. In some embodiments, the solvent is an alcohol. Examples of alcohols include $C_1$-$C_4$ alcohols, such as methanol, ethanol, propanol and butanol. In some embodiments, an alcohol solvent can be the same as the diol being formed by treating the PHA.

In embodiments in which a solvent is used, the concentration of PHA in the solvent is at least about five weight percent (e.g., at least about 10 weight percent). In some embodiments, the concentration of PHA in the solvent is at most about 90 weight percent (e.g., at most about 50 weight percent). For example, the concentration of PHA in the solvent can be from about five weight percent to about 90 weight percent (e.g., from about five weight percent to about 90 weight percent).

In certain embodiments, the PHA can be treated while using relatively little solvent (e.g., relatively little halogenated solvent) other than the alcohol. For example, the total amount of solvent other than the alcohol present during the treatment of the PHA to form the ester can be less than one milliliter (e.g., less than about 0.9 milliliter, less than about 0.8 milliliter, less than about 0.7 milliliter, less than about 0.6 milliliter, less than about 0.5 milliliter, less than about 0.4 milliliter, less than about 0.3 milliliter, less than about 0.2 milliliter, less than about 0.1 milliliter, less than about 0.05 milliliter, about zero milliliter) per gram of PHA.

Generally, in embodiments in which hydrogen is used as the reducing species, elevated pressure is used. In some embodiments, the pressure (e.g., hydrogen pressure) used is at least about 200 psig (e.g., at least about 500 psig, at least about 1000 psig, at least about 2500 psig, at least about 3000 psig). In certain embodiments, the pressure (e.g., hydrogen pressure) is at most about 5000 psig (e.g., at most about 4000 psig). Other gases (e.g., nitrogen) may be used in addition to hydrogen.

In embodiments in which the PHA treatment to form the diol is performed in the presence of a catalyst, the catalyst is typically a metal catalyst. Examples of catalysts include copper chromite catalysts, platinum catalysts, (e.g., 2,4-Pentanedionate Platinum (II), Dichloro(norbornadiene) platinum (II)), palladium catalysts (e.g., Palladium (II) Acetate Trimer, Tris(dibenzylideneacetone)dipalladium(0), trans-Dichlorobis(triphenylphosphine)palladium (II)), nickel complexes, rainey nickel, ruthinium catalysts (e.g., ruthinium dichloride bis-(triphenylphosphine)(1,2-ethanediamine), ruthinium dichloride bis-(tri-p-tolylphosphine)(1,2-ethanediamine)), cobalt, rhodium catalysts (e.g., 2,4-Pentanedionate rhodium, Rhodium (III), Chloro (norbornanediene)rhodium (I) Dimer, Rhodium (II) Octanoate Dimer), Iridium catalysts (e.g., 2,4-Pentanedionate Iridium (III) and Hydridocarbonyltris(triphenylphosphine)iridium (I)).

Generally, in embodiments in which a catalyst is used, the amount of catalyst can be selected as desired. In some embodiments, the catalyst can be at least about 0.1 weight percent (e.g., at least about 0.25 weight percent, at least about 0.5 weight percent, at least about one weight percent) of the total amount of PHA present when the catalyst is added. In certain embodiments, the catalyst can be at most about 10 weight percent (e.g., at most about five weight percent, at most about three weight percent) of the total the total amount of PHA present when the catalyst is added. For example, the catalyst can be from about 0.1 weight percent to about 10 weight percent (e.g., from about 0.25 weight percent to about five weight percent of the total the total amount of PHA present when the catalyst is added.

In embodiments in which the PHA treatment to form the diol is performed in the presence of a reducing agent, the reducing agent can be an active metal hydride. Examples of reducing agents include lithium aluminum hydride, sodium aluminum hydride, sodium borohydride and Vitride (Zealand Chemicals).

In general, at least about two (e.g., at least about 2.5, at least about three) equivalents of reducing agent are used per mole of PHA monomer unit converted to diol.

In certain embodiments, the amount of undesired byproducts is relatively small. For example, alkenoic byproducts can be undesired. In some embodiments, the percent yield of undesirable byproducts (e.g., alkenoic byproducts) from the PHA is less than about 10% (e.g., less than about eight percent, less than about five percent, less than about three percent, less than about one percent).

In some embodiments, the methods result in a relatively high yield of the diol. For example, the percent yield of the diol from the PHA can be at least about 30% (e.g., at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%).

In embodiments in which the PHA is a chiral PHA, the diol can be a chiral diol, and the percent chirality yield of chiral diol can be relatively high. For example, the percent chirality yield of a chiral diol from a chiral PHA can be at least about five percent (e.g., at least about 10%, at least about 25%, at least about 50%, at least about 75%, at least about 85%, at least about 90%, at least about 95%, at least about 98%).

The diols can be used in a variety of applications. As an example, a diol can be used in aromatic polyester production. As another example, chiral diols (e.g., the D-isomer of 1,3-butanediol from poly 3-hydroxybutyrate) can be used in pharmaceutical derivatives and/or nutraceutical derivatives (e.g., via the reaction of chiral 1,3-butanediol with chiral D-3-hydroxybutyrate and/or acetoacetate to provide a chiral ester). As a further example, 1,4-butanediol (e.g., from poly 4-hydroxybutyrate) can be useful in the production of aromatic polyesters, tetrahydrofuran, gamma butyrolactone, aliphatic polyesters, urethanes and elastomers. As an additional example, 1,6-hexane diol (e.g., from poly 6-hydroxyhexanoate) is commonly used in polyurethanes and polyester resins. 1,3-butanediol, 1,3-pentanediol and/or 1,3- hexanediol can also be combined with diacids (e.g., adipic acid, terephthalic acid, succinic anhydride) to form polyester resins.

Alkenoic Acids

In general, treating a PHA to form an alkenoic acid (e.g., a 1,2-unsaturated acid, a 2,3-unsaturated acid) includes heating the PHA.

Typically, the PHA is heated to a temperature of at least about 100° C. (e.g., at least about 150° C., at least about 200° C., at least about 250° C.). In certain embodiments, the PHA is heated to a temperature of at most about 300° C.

Generally, the pressure used when heating the PHA can be selected as desired. As an example, the PHA can be heated at atmospheric pressure (e.g., while exposed to air or inert gas). As another example, the PHA can be heated at elevated pressure.

In certain embodiments, an alkenoic acid formed by treating a PHA has the structure:

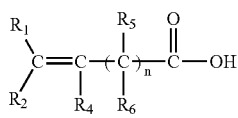

Examples of alkenoic acids include acrylic acid, crotonic acid, pentenoic acid, octenoic acid, ethyl crotonate, methyl crotonate, butyl crotonate, 2-ethylhexyl crotonate, ethyl 2-octenoate, ethyl 2 pentenoate, ethyl 2-decanoate and vinyl acetic acid.

In certain embodiments, the PHA can be treated while using relatively little or no solvent (e.g., relatively little halogenated solvent). For example, the total amount of solvent present during the treatment of the PHA to form the alkenoic acid can be less than one milliliter (e.g., less than about 0.9 milliliter, less than about 0.8 milliliter, less than about 0.7 milliliter, less than about 0.6 milliliter, less than about 0.5 milliliter, less than about 0.4 milliliter, less than about 0.3 milliliter, less than about 0.2 milliliter, less than about 0.1 milliliter, less than about 0.05 milliliter, about zero milliliter) per gram of PHA.

In some embodiments, an alkenoic acid can be formed from the PHA at a relatively high percent yield. For example, the percent yield of alkenoic acid from the PHA can be at least about 50% (e.g., at least about 60%, at least about 70%, at least about 80%, at least about 90%, at least about 95%, at least about 98%). In some embodiments, these percent yields of alkenoic acid are achieved using PHA derived from biomass when less than about 50 weight percent (e.g., less than about 40 weight percent, less than about 30 weight percent, less than about 20 weight percent, less than about 10 weight percent, less than about weight percent five weight percent, less than about three weight percent, less than about one weight percent, about zero weight percent) of the PHA that is treated to form the alkenoic acid is removed from the biomass before being treated to form the alkenoic acid.

The methods can further include isolating at least a portion of the alkenoic acid formed by treating the PHA. For example, in embodiments in which the PHA is derived from biomass and the PHA is not removed from the biomass before being treated to form the amide, the methods can include removing at least a portion (e.g., at least about 10 weight percent, at least about 20 weight percent, at least about 30 weight percent, at least about 40 weight percent, at least about 50 weight percent, at least about 60 weight percent, at least about 70 weight percent, at least about 80 weight percent, at least about 90 weight percent, at least about 95 weight percent, at least about 98 weight percent) of the alkenoic acid from the biomass. In some embodiments, the temperatures used (e.g., at least about 200° C.) volatilize the alkenoic acid.

In embodiments where the PHA is a copolymer, different alkenoic acids can be formed corresponding to the different monomer units in the PHA copolymer. As an example, the PHA can be poly 3-hydroxybutyrate-co-3-hydroxyvalerate, and the alkenoic acids can be crotonic acid, pentenoic acid, 2-pentenoic acid, 2-butenoic acid and/or 2 octenoic acid.

The alkenoic acids can be used in various applications.

In some embodiments, an alkenoic acid can be used in a polymerization process (e.g., a free radical polymerization process) to form a useful material. As an example, crotonic acid can be used in a free radical polymerization process to form a vinyl acetate-crotonate copolymer for use in hair spray formulations. As another example, acrylic acid can be used within polymerization processes to produce polyacrylate resins for use in paints, adhesives, coatings, thickeners (e.g., aqueous thickeners), resins (e.g., thermoplastic resins) and modifiers (e.g., impact modifiers).

The following examples are illustrative and not intended as limiting.

EXAMPLE 1

Ethyl-3-hydroxybutyrate was prepared from a PHA (poly 3-hydroxybutyrate) as follows. A solution of 1.0 g of poly 3-hydroxybutyrate (94% purity) in 4.0 ml of absolute ethanol was prepared in a glass pressure bottle. The PHA was derived from biomass. 10.5 mg of di-butyl tin oxide and 0.5 ml of diphenylmethane were added as a catalyst and as an internal gas chromatographic standard, respectively. The mixture was heated to 180° C. with magnetic stirring. After 2.0 hours the percent yield of ethyl-hydroxybutyrate from the PHA was 77.8%, and after 4.0 hours the percent yield of ethyl-hydroxybutyrate from the PHA was 92%.

EXAMPLE 2

Example 1 was repeated at 200° C., and after two hours of reaction time the percent yield of ethyl-3-hydroxybutyrate from the PHA was 82.2%.

EXAMPLE 3

Example 2 was repeated except that 10.5 mg of titanium tetra-isopropoxide was used as the catalyst. After two hours of reaction time, the percent yield of ethyl-3-hydroxybutyrate from PHA was 82.2%.

EXAMPLE 4

N-methyl 4-hydroxybutyramide was prepared by treating a PHA (poly 4-hydroxybutyrate) as follows. A 300 ml 316 stainless steel autoclave equipped with a stirrer, a gas inlet line, a vent line and a rupture disc was charged with 13.1 g of poly 4-hydroxybutyrate and 20 g of methylamine. The PHA had been isolated from biomass. The autoclave was: flushed with nitrogen; put under 100 psig of nitrogen; heated with stirring to 80° C.; and held at this temperature for 5.0 hours. The autoclave was then cooled to room temperature, vented and opened. The PHA was completely consumed. The excess methylamine was removed under a nitrogen stream, and the remaining dark brown liquid analyzed via gas chromatography (GC). The GC trace on a boiling point column showed only one component, and that point corresponded to N-methyl 4-hydroxybutyramide.

EXAMPLE 5

N-Methylpyrrolidone was prepared as follows. The liquid from Example 4 was heated under nitrogen with stirring in the same autoclave to 280° C. and held at that temperature for two hours. The pressure was 600 psig. After cooling, the clave was opened and the liquid contents discharged and analyzed via GC. The majority of the liquid was methylpyrrolidone, and the remainder of the liquid was unreacted amide having the same retention time as the starting amide. At 100% polymer conversion, the percent yield of methylpyrrolidone from PHA was in excess of 90%.

EXAMPLE 6

1,4-Butanediol was prepared from a PHA (poly 4-hydroxybutyrate) as follows. A one liter autoclave was charged with 40 g of poly 4-hydroxybutyrate, 400 g of methanol and 5.0 g of powdered barium promoted copper chromite obtained from Engelhard. The PHA had been isolated from biomass. The clave was pressured with hydrogen to 200 psig and the pressure was released. This was done four times and the clave then pressured to 2000 psig with hydrogen. The clave was then heated with stirring to 160° C. and the final pressure adjusted to 3500 psig with hydrogen. The clave was kept at 160° C. for 2.0 hours, and the temperature then raised to 180° C. for an additional 2.0 hours. The pressure was adjusted to 3500 psig. Finally, the temperature was raised to 200° C. for an additional 2.0 hours, again at 3500 psig hydrogen. The clave was then cooled to room temperature and vented. Any remaining hydrogen was purged with nitrogen and the contents discharged. There was no solid PHA left, and the solution was water white. Analysis of the solution by GC after filtering off the catalyst showed that the major product was 1,4-butanediol.

EXAMPLE 7

Crotonic acid was prepared from a PHA (poly 3-hydroxybutyrate) as follows. Seven grams of biomass (with most water removed, but non-lyophilized) from the fermentation process of poly 3-hydroxybutyrate (comprising 4.3 g poly 3-hydroxybutyrate having a molecular weight>700,000, 2.1 g of cell components and 0.6 g of inorganic salts remaining from the fermentation media) was heated at 245° C. in an air atmosphere. After 30 minutes, no further volatile components were observed. The volatile component was analyzed by GC. The yield of alkenoic acid component was 98.0% based on the poly 3-hydroxybutyrate component of the biomass. The composition of the alkenoic acid fraction was 96% crotonic acid, and no unsaturated dimer or trimer was detected.

EXAMPLE 8

Crotonic acid was prepared from a PHA (poly 3-hydroxybutyrate) as follows. Eight grams of biomass (with most water removed, but non-lyophilized) from the fermentation process of poly 3-hydroxybutyrate washed free of soluble inorganic salts (comprising 5.7 g poly 3-hydroxybutyrate having a molecular weight>700,000, 2.3 g of cell components) was heated at 245° C. in an air atmosphere. After 30 minutes no further volatile components were observed. The volatile component was analyzed by GC. The yield of the alkenoic acid component was 96.8.0% based on the poly 3-hydroxybutyrate component of the biomass. The composition of alkenoic acid fraction: 95.5% crotonic acid, and no unsaturated dimer or trimer was detected.

EXAMPLE 9

2-ethylhexyl R-3-hydroxybutyrate was prepared from a PHA (ethyl R-3-hydroxybutyrate) as follows. 132 g of ethyl R-3-hydroxybutyrate were combined with 130 g of 2-ethylhexanol and 0.5 g of sulfuric acid catalyst. The mixture was heated to a temperature of 140° C. for 2 hours, and the ethanol removed by fractional distillation. Gas chromatography (GC) identified the resultant product as being 98% pure 2-ethylhexyl R-3-hydroxybutyrate with the following properties: boiling point at atmospheric pressure: 495–502° F.; flash point (closed cup): 260° F.; kinematic viscosity: 11.06 cSt; and relative evaporation rate: <0.01 (butyl acetate=1).

EXAMPLE 10

Cyclohexyl R-3-hydroxybutyrate was prepared from a PHA (poly-R-3-hydroxybutyrate) as follows. 900 mL of cyclohexanol, 200 grams of poly-R-3-hydroxybutyrate and 5.26 grams of dibutyl-tin oxide were reacted at 142–147° C. for 8 hours. The crude brown product was filtered and short-path distilled. The first distillate was 560 mL of pure cyclohexanol. The second distillate was clear cyclohexyl ester with purity by GC of 97.6% and had the following physical properties: boiling point at atmospheric pressure: 485–502° F.; flash point (closed cup): 255° F.; kinematic viscosity: 28.87 cSt; relative evaporation rate: <0.01 (butyl acetate=1).

EXAMPLE 11

4-methylcyclohexyl R-3-hydroxybutyrate was prepared from poly-R-3-hydroxybutyrate as follows. 900 mL of methylcyclohexanol, 200 grams of poly-R-3-hydroxybutyrate and 5.26 grams of dibutyl-tin oxide were reacted at 142–147° C. for 8 hours. The crude brown product was filtered and short-path distilled. The first distillate was 560 mL of pure methylcyclohexanol. The second distillate was clear methylcyclohexyl ester with purity by GC of 97.6% and had the following physical properties: boiling point at atmospheric pressure: 459–485° F.; flash point (closed cup): 262° F.; kinematic viscosity: 30.49 cSt; and relative evaporation rate: <0.01 (butyl acetate=1).

Evaluation of Examples 9 Through 11 in Coating Systems

The following evaluation was performed independently for each of the solvents prepared in Examples 9–11. The solvent was slowly added to 50 g of emulsion under continuous stirring for at least 10 minutes. The stability of the system was determined by allowing the emulsion to stand for 24 hours and the consistency visually determined to see if any phase separation or gel formation had developed.

The glass transition temperature (Tg) for the polymer, and the blends was determined by placing a small sample of the emulsion onto a glass plate and allowing the water to evaporate. The dried material was then transferred to a Perkin Elmer DSC and heated from −50° C. to +100° C. at 10° C./minute. The mid point glass transition temperature was determined from the inflection in the heat capacity versus temperature curve.

Film forming properties were determined by storing the emulsion in a refrigerator at 5° C. overnight with a number of clean glass plates. A wet polymer film approximately 100-200 microns in thickness was applied to the glass plates which were then stored again in the refrigerator for several days. After this time period, the films were examined for integrity and strength.

| Polymer grade | solvent | phr on dry polymer | stability | Tg (C.) | Film forming properties 5C |
|---|---|---|---|---|---|
| Airflex 30 | None | None | stable | +32 | No film, powdery |
| Polyvinyl acetate | Ex. 9 | 3.2 | stable | −5.2 | Tough clear film |
| | Ex. 9 | 6.8 | stable | −11.1 | Tough clear film |
| | Ex. 10 | 3.2 | stable | −4.6 | Tough clear film |
| | Ex. 11 | 3.5 | stable | −4.9 | Tough clear film |
| Airflex 4514 | None | None | stable | 69.4 | No film, powdery |
| Polyvinyl chloride | Ex. 9 | 3.2 | stable | 10.2 | No film, powdery |
| | Ex. 9 | 7.2 | stable | −7.2 | Tough clear film |
| | Ex. 9 | 14.8 | stable | −15.2 | Tough clear film |
| Nacrylic 2500 | None | None | stable | 24 | No film, powdery |
| Acrylic copolymer | Ex. 9 | 7.2 | stable | −5.2 | Tough clear film |
| | Ex. 9 | 14.4 | stable | −24.4 | Tough clear film |
| Nacrylic 6408 | None | None | stable | 52 | No film, powdery |
| Acrylic copolymer | Ex. 9 | 8.6 | stable | 2.3 | Tough slightly opaque film |
| | Ex. 9 | 14.4 | stable | −24.3 | Tough clear film |

Other embodiments are in the claims.

The invention claimed is:

1. A method of forming acrylic acid, comprising: heating a PHA derived from a biomass to form the acrylic acid.

2. The method of claim 1, wherein the PHA is poly 3-hydroxypropionate or a 3-hydroxypropionate containing polymer.

3. The method of claim 1, wherein the PHA is a copolymer and contains at least one 3-hydroxypropionate monomer.

4. The method of claim 1, wherein the PHA is heated to at least about 100° C.

5. The method of claim 1, wherein the PHA is heated to at least about 150° C.

6. The method of claim 1, wherein the biomass selected from the group consisting of plant biomass and microbial biomass.

7. The method of claim 1, wherein less than about 50 weight percent of the PHA that is treated to form the acrylic acid is removed from the biomass before being treated to form the acrylic acid.

8. The method of claim 1, further comprising continuously removing at least some of the acrylic acid.

9. The method of claim 1, wherein the percent yield of the acrylic acid from the PHA is at least about 50%.

10. The method of claim 1, wherein the percent yield of the acrylic acid from the PHA is at least about 60%.

11. The method of claim 1, wherein the percent yield of the acrylic acid from the PHA is at least about 70%.

12. The method of claim 1, wherein the percent yield of the acrylic acid from the PHA is at least about 80%.

13. The method of claim 1, wherein the percent yield of the acrylic acid from the PHA is at least about 90%.

14. The method of claim 1, wherein the biomass comprises a microbial strain selected from the group consisting of *Ralstonia eutropha, Alcaligenes latus, Azotobacter, Aeromonas, Comamonas, Pseudomonads, Escherichia coli*, and *Klebsiella*.

15. The method of claim 1, wherein the biomass is a bacterial biomass, a yeast biomass, or a fringal biomass.

* * * * *